United States Patent

Aicher et al.

[11] 3,994,977
[45] Nov. 30, 1976

[54] MANUFACTURE OF FORMALDEHYDE

[75] Inventors: Albrecht Aicher, Frankenthal; Hans Haas, Ludwigshafen, both of Germany; Oskar Hussey, deceased, late of Ludwigshafen, Germany, by Hedwig Stephanie Hussey, representative of the heirs; Hans Diem, Ludwigshafen, Germany; Guenther Matthias, Ludwigshafen, Germany; Gunter Lehmann, Ludwigshafen, Germany

[73] Assignee: BASF Aktiengesellschaft, Ludwigshafen (Rhine), Germany

[22] Filed: May 10, 1974

[21] Appl. No.: 468,872

[30] Foreign Application Priority Data

May 11, 1973  Germany............................ 2323758

[52] U.S. Cl. ........................ 260/603 R; 260/643 D; 202/158; 261/114 R; 23/263; 203/49
[51] Int. Cl.²......................................... C07C 45/16
[58] Field of Search..................... 260/603 R, 643 D

[56] References Cited
UNITED STATES PATENTS

| | | |
|---|---|---|
| 2,772,081 | 11/1956 | Hibshman et al................... 202/158 |
| 2,819,049 | 1/1958 | Manning, Jr. et al............... 202/158 |
| 2,853,281 | 9/1958 | Hibshman et al................... 202/158 |
| 2,960,322 | 11/1960 | Eld..................................... 202/158 |

OTHER PUBLICATIONS

Carlson, et al., Distillation, vol. IV, Interscience Publishers, pp. 469–476 (1965).
F.I.A.T. Report 999, Apr. 2, 1947.
Walker, Formaldehyde, 3rd Edition, pp. 8–24 (1967).

*Primary Examiner*—James O. Thomas, Jr.
*Assistant Examiner*—G. Breitenstein
*Attorney, Agent, or Firm*—Johnston, Keil, Thompson & Shurtleff

[57] ABSTRACT

Manufacture of formaldehyde by oxidative dehydrogenation of methanol in the presence of a silver catalyst, wherein methanol and water are evaporated in the presence of air in a plate column containing a number of double plates each consisting of a sieve plate and a lower plate having the form of a shallow bowl and inclined at a specific angle to the horizontal, the resulting vaporous mixture then being reacted. The formaldehyde which may be produced by the process of the invention is a disinfectant, tanning agent, reducing agent and a valuable starting material for the manufacture of synthetic resins, adhesives and plastics.

7 Claims, 1 Drawing Figure

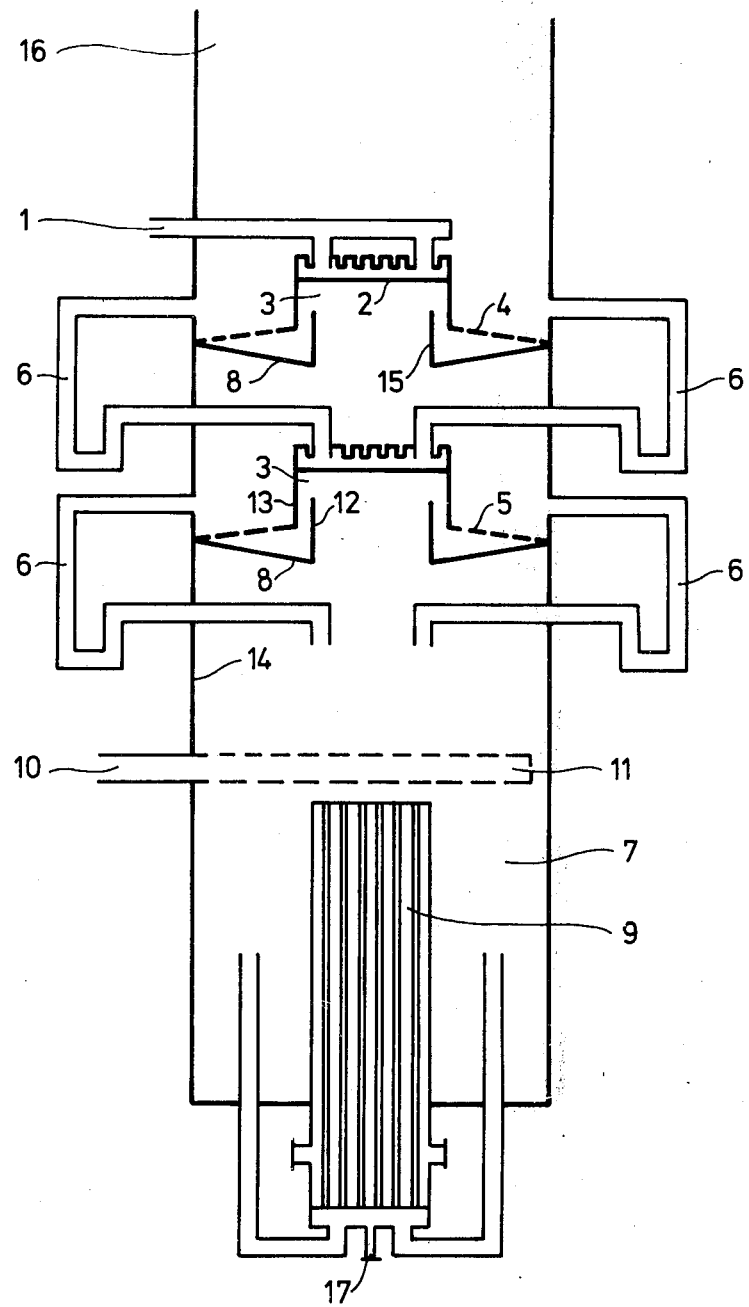

MANUFACTURE OF FORMALDEHYDE

This invention relates to a process for the manufacture of formaldehyde by oxidative dehydrogenation of methanol in the presence of a silver catalyst, wherein methanol and water are evaporated in the presence of air in a plate column having a plurality of double plates each consisting of a sieve plate and a lower plate having the form of a shallow bowl and inclined at a specific angle to the horizontal, the resulting vaporous mixture then being reacted.

Ullmanns Encyklopaedie der technischen Chemie, Vol. 7, pp. 659 et seq., describes various processes for the manufacture of formaldehyde by oxidative dehydrogenation of methanol in the presence of a silver catalyst at elevated temperature. The starting material is pure methanol obtained from crude methanol by fractional distillation. Crude methanol, depending on its method of manufacture (Ullmanns Encyklopaedie der technischen Chemie, Vol. 12, pp. 398 et seq.), varies in its composition and generally contains from 95 to 70% w/w of methanol, from 1 to 29% w/w of water and from 0.1 to 6% w/w of impurities. Depending upon manufacture and storage, the impurities may be, for example, alkali metal salts such as sodium formate, sodium hydrogen carbonate, sodium carbonate, sodium acetate, sodium sulfide; sodium or sodium methoxide, potassium hydroxide, sodium hydroxide, formic acid; aldehydes such as acrolein, glyoxal, butyraldehyde, propionaldehyde, acetaldehyde, ketones such as acetone and butanone-2; glycol, diglycol, triglycol and higher alkanols such as n-butanol, isobutanol, isopropanol, n-propanol, n-pentanol, isohexanol, isoheptanol, n-hexanol; ethers such as glycol methyl ether, diglycol methyl ether, dimethyl ether; aliphatic, cycloaliphatic, aromatic hydrocarbons such as benzene, toluene, xylene, decane, undecane, dodecane, cyclohexane, ethyl benzene; organic or inorganic compounds such as formates, sulfide of metals such as iron, chromium, copper, aluminum, zinc, magnesium; sulfur compounds such as dimethyl sulfide; esters such as dimethyl terephthalate; amines such as monomethylamine, dimethylamine, trimethylamine; and ammonia. In particular, alkaline impurities are usually present, since the acid present in methanol is neutralized with alkalis in almost synthesis processes.

In the usual methods, when the strongly effervescing crude methanol evaporates, not only vapors but also liquid and solid impurities pass into the vaporous starting mixture for the formaldehyde synthesis, for example in the form of fine droplets or fine particles of solids or as a liquid mist. They give rise to side reactions during reaction of the methanol or attack the catalyst, for example by destroying the active surface of the silver or by depositing solids or resinous substances onto the catalyst and thus reducing its life and consequently the yield of product and the economic efficiency of the process. Furthermore, deposits may cause blockage of pipelines or corrosion of the metal surfaces and thus interfere considerably with the operation of a plant. The catalyst, consisting of granules of silver, gradually loses its permeability to gases on account of the deposits. The pressure drop across the catalyst bed rises and demands a higher energy output by the air compressors. The blowers generally used are no longer capable of providing the required stream of air and the output of the plant falls, which makes it necessary to switch off the plant prematurely, in order to renew the catalyst. This is another cause of losses of yield. Moreover, a shorter life of the catalyst entails additional costs involved in changing and regenerating the catalyst.

Another cause of catalyst poisoning lies in the effect of harmful foreign substances contained in the air used for the oxidation. Such air impurities occur to a particularly great extent in concentrated industrial areas and comprise, for example, the following components which are toxic to the catalyst used: hydrogen sulfide, sulfur dioxide, hydrogen chloride, hydrogen fluoride, halogens, volatile halo compounds such as carbon tetrachloride; ammonia, amines such as monomethylamine, dimethylamine, trimethylamine; arsenic and antimony compounds such as arsenic trioxide, antimony trioxide; acetylene, phosphorus compounds such as hydrogen phosphide; lamp black; iron oxide dust; hydrogen cyanide; carbon monoxide; foreign substances resulting from the anaerobic decomposition of protein waste products, for example mercaptans, indol, skatole; nitrogen oxides; lead compounds such as tetraethyl lead and tetramethyl lead; organic compounds such as 3,4-benzpyrene, fluoranthrene, pyrene, phenanthrene, passing into the air from automobile exhaust gases, and their oxidation products such as acrolein. In general, the proportion of foreign substances in the air is from 0.01 to 10 ppm.

Ullmanns Encyklopaedie der technischen Chemie, Vol. 7 (loc. cit.) also describes the use of methanol in the form of an aqueous solution, for example a 55% w/w aqueous methanol solution, and evaporating this in an evaporator, mixing the vapor with air and then effecting oxidative dehydrogenation of the methanol in contact with a silver catalyst. The water used is condensed water and also chlorine-free and, advantageously, softened water. The water which may be used for this purpose includes ground water, spring water, surface water such as river water, drinking water, boiler feed water and, in some cases, sea water. Depending on the source and preparation of such waters, they may contain numerous substances as impurities, for example metal salts such as manganese sulfate, iron chloride, alkaline earth metal compound in the form of water hardness, ammonium salts, alkali metal salts, metals such as zinc or aluminum or copper from, say, the materials of the pipes used, nitrates, silicates, nitrites, fluorides, phosphates and organic decomposition products such as phenols.

The evaporation of such mixtures of methanol and water often gives rise to difficulties, frequently of a serious nature. The rate of vaporization falls, the liquid is retained in the evaporator and large amounts of foam form at the surface of the evaporating methanol solution, which foam has relatively large bubbles and is usually of a relatively solid consistency. At the same time, the pressure in the evaporator may increase and the liquid mixes with the air to form, in time, a dense layer of foam. In some cases the foam is entrained and thus comes into contact with the catalyst and impairs or even prevents conversion of the methanol. In industrial plants, where generally from 1,000 to 20,000 kg of a 60-95% w/w methanol solution are evaporated per hour, the pressure may rise from the usual value of 1.2 atmospheres to from 1.5 to 1.8 atmospheres after a period of from 1 to 16 hours and frequently of from only 1 to 3 hours, when a two-plate vaporizing column is used. At the same time, the rate of evaporation of the solution falls to from 70–80% of its original value. All of these difficulties lead to usually considerable trouble and even stoppages. At the least it is necessary to stop operation for the control of the input and of the heat applied.

Austrian Pat. No. 218,492 discloses an air purifying method in which air is passed through dust filters and is then washed with 5–10% aqueous caustic soda solution and subsequently subjected to a methanol wash, a potassium permanganate wash and a water wash. The said patent explains that this method of purification is complicated, expensive and ineffective and teaches an air purifying technique using as washing liquid an aqueous formaldehyde solution such as is obtained in the formaldehyde plant. But this method of purification is also unsatisfactory in large-scale work. Since, in order to avoid the formation of polymers, the temperature of a 40% formaldehyde solution must be at least 50° C, such a solution has a considerable vapor pressure. The vapor pressure of formaldehyde solutions increases steeply with increasing formaldehyde content and is 6.3 mm of Hg for a 40% w/w solution at 55° C and 15.3 mm of Hg for a 50% w/w solution at 60° C. At a rate depending on this vapor pressure, formaldehyde is entrained by the air, which is not conducive to simple and economical operation and reduces the yield of product. The entrained formaldehyde is decomposed at the silver catalyst to form carbon monoxide, methanol and other by-products (Journal of Chemical Physics 19, pp. 176 et seq. (1959); Recueil 58, pp. 39 et seq. (1939)). When the air is very impure, the impurities pass into the formaldehyde solution to a marked degree, and this can cause trouble in further processing. Acidic foreign substances in the air are not washed out well, since the formaldehyde solution is itself acidic.

Industrial and Engineering Chemistry, Vol. 44, p. 1514 (1952) discloses a method of washing the reaction air with 5% aqueous caustic soda solution for the removal of foreign substances. An article in Chemical Engineering 1949, p. 132 and one in Ullmanns Encyklopaedie der technischen Chemie, Vol. 7, p. 660 also mention air washing with caustic soda solution or soda solution. The washing towers used have a height of from 3 to 6 meters. The purifying efficiency of these processes is still unsatisfactory, particularly in the case of large air throughputs in industrial plants. The apparatus for evaporating the methanol is generally provided with demisters (B.I.O.S. Final Report No. 1,331; F.I.A.T. Final Report No. 999), e.g. Raschig ring packings or packings of wire gauze. Such packings are reasonably efficient until they contain a certain amount of liquid. From then on, some of the liquid passes through and atomizes beyond the packing to form droplets or a mist. Thus it is not possible to prevent the formation of extensive deposits on the catalyst by these measures. For the above reasons, it has not been possible to use crude methanol for the manufacture of formaldehyde on a large scale.

From German Pat Nos. 1,235,881 and 1,136,318 and German published application No. 1,277,834 it is known that it is industrially possible to use crude methanol as starting material if it is purified by distillation by the removal of a low-boiling fraction or if it is treated with alkalis and/or oxidizing agents. These processes save the expensive and time-consuming fractional distillation of methanol. Despite the advantages of these processes, the life of the catalyst and the yields and space-time yields of pure product obtained therewith are still unsatisfactory, since some of the impurities contained in the crude methanol, particularly the alkaline compounds, are not separated and de-activate the catalyst during the reaction.

B.I.O.S. Reports Nos. 778 and 1,331 both describe simple evaporators, into which air is passed through a perforated tube. The above drawbacks occur in both processes. At the base of the evaporator, high-boiling impurities collect and must be withdrawn, in which case from about 3 to 5% of the total methanol in the mixture is lost. Thus it is not possible to use crude methanol in such methods. If alkali were added, as is advantageous in the case of crude methanol, it would be necessary to withdraw material continuously from the base of the evaporator.

In F.I.A.T. Report No. 999, pp. 2, 5 and 13, there is described an evaporator in which the water/methanol mixture is passed upward into the base of the evaporator and is evaporated. The vapor is passed through two bubble-cap plates. The bubble caps are heated by means of steam coils. This arrangement is intended to superheat the vapor mixture so as to avoid condensation at subsequent points. Furthermore, this apparatus serves to improve mixing of the vapors and air. The description shows that the bubble-cap plates can have no separating effect, since refluxing is impossible due to the superheating of the vapors. The aforementioned drawbacks caused by the impurity of the starting materials also occur in this process.

In addition, the prior art processes give rise to trouble when the evaporating plants are put into operation, especially after interruptions or stoppages of the plants. In such cases, air is available very quickly, since the blowers rapidly rev up to full output. However, heating of the evaporator costs valuable time. Thus it is necessary to have relatively large quantities of liquid present on each plate to act as heat-storage means, to provide heat for evaporation when required quickly. However, bubble-cap plates and packed columns empty very rapidly. Sieve-plate columns of conventional design are also of little assistance in this case, since they are sensitive to variations in throughput and also require a relatively long period for heating up. Indeed, they are inclined to cause difficulties when the vapor passes through the perforations, since the liquid collecting on the plates tends to be entrained by the vapor in the form of drops, or it frequently blocks up the perforations and drips through. Valve-tray columns are expensive and offer high resistance at high throughputs. Moreover, after relatively long on-stream periods, the valves no longer close completely, with the result that these columns also empty very rapidly. Furthermore, the throughput is particularly high in such synthesis processes, since the vapor mixture and air serve as starting mixture for the formaldehyde synthesis. When a plant is started, the gas mixture consisting of air and vapor bubbles through the liquid in the evaporating chamber only very slowly, for the reasons given above. There is insufficient or no exchange between the vapor and liquid, as mixing is not thorough. The result is considerable accumulation of methanol in the base of the evaporator and consequently increased pollution of the waste water, which causes environmental problems and reduces the economical efficiency of the process. Finally, it must be ensured at all times, including at low throughputs, that an adequate amount of methanol evaporates during the passage of air, since otherwise mixtures rich in air will be formed, which mixtures are explosive. Thus, for the above reasons, any stoppage of the plant calls for special measures for restarting.

The invention relates to a novel process for the manufacture of formaldehyde in good yield and purity and in a simpler and more economical manner.

We have now found that formaldehyde may be advantageously obtained by oxidative dehydrogenation of methanol in admixture with water vapor and air and in the presence of a silver catalyst at elevated temperature, if methanol and water are evaporated with admixture of air in a plate column having a plurality of bubble-cap sieve plates, each of which has an upper sieve plate which slopes downwardly toward its periphery and has a perforation diameter of from 2 to 15 mm and a lower plate in the form of a shallow bowl sloping upward toward its periphery, the angle of slope of the sieve plate to the horizontal being from 2° to 10° and that of the lower plate being from 4° to 20°, the liquid substances being fed to the top and air to the bottom of the column and the resulting vaporous starting mixture being subjected to oxidative dehydrogenation.

The invention is based on the fact that trouble-free continuous operation is not dependent on one measure alone, for example a specific method of purifying the starting materials or the maintenaince of a specific space velocity, but requires a combination of interrelated factors. In such a combination, the evaporation of methanol and water and the admixture of these vapors with air in the plate column of the invention are of particular importance. Compared with the prior art processes using pure methanol, the process of the invention produces formaldehyde in good yield and purity in a simpler and more economical manner. Compared with the prior art syntheses using crude methanol as starting material, the process of the invention gives formaldehyde in better yields, space-time yields and purity and the life of the catalyst is longer. Mists, finely divided solids and droplets of corresponding solutions are substantially separated. The aforementioned disadvantages and difficulties are obviated. Accordingly, the life of the catalyst is prolonged. Rapid poisoning of the catalyst by the reaction air, crude methanol or reaction water and associated accumulation of foreign substances in the solution of the product are avoided. Starting of a plant for the first time or after a stoppage is simpler, quicker and less troublesome and the standstill period of a plant cause by catalyst poisoning or trouble in the evaporator is reduced. The process of the invention is particularly advantageous as regards environmental protection and operational safety. If the starting materials contain portions of high-boiling by-products, separation thereof is simpler, quicker and more complete owing to the good separating action of the plate column of the invention. All of these advantageous results are surprising in the light of the prior art.

Suitable starting materials for the process are pure methanol, technical methanol or crude methanol, all produced by a high-pressure or low-pressure process, in admixture with water. The concentration of the aqueous mixtures my conveniently be from 60 to 95% by weight and preferably from 70 to 90% by weight of methanol. In one advantageous embodiment, use is made of crude methanol which has been purified by one or other of the processes described in German published application No. 1,277,834, German Pat. No. 1,235,881 and German Pat. No. 1,136,318 by separation of a low-boiling fraction or by treatment with oxidizing agents and/or alkalis.

The methanol is fed to the reaction chamber in vapor form in admixture with water vapor, air and, if desired, an inert gas. A suitable inert gas for the process is for example nitrogen. Methanol, water and air are reacted in the form of a vaporous or gaseous starting mixture conveniently in a ratio of from 0.25 to 0.60 and preferably from 0.35 to 0.5 mole of oxygen (in the form of air) per mole of methanol and from 0.2 to 2 and preferably from 0.3 to 1.2 moles of oxygen (in the form of air) per mole of water. The rate of feed of the liquid or air to the evaporator is regulated in such a manner that the mixture leaving the evaporator and passing to the reaction chamber has a composition corresponding to the above molar ratios. Advantageously, throughputs of from 1.2 to 5.0 tons of aqueous methanol solution and from 1.3 to 55 tons of air per hour per square meter of column cross-section are used.

Advantageously, evaporation is carried out in plate columns having a height of from 1.5 to 7 meters and especially from 2 to 4 meters (as measured from the surface of the bottoms) and a diameter of from 1 to 3 meters and in particular from 1.6 to 2.5 meters and having from 2 to 6 and preferably 2, 3 or 4 bubble-cap sieve plates separated from each other vertical distances of advantageousy 30 to 90 cm and preferably from 40 to 70 cm. Advantageously, each bubble-cap sieve plate has an upper part in the form of a circular cap with sieve plate attached thereto and a lower plate in the form of a shallow bowl of which the center is in the form of a round open chimney, whilst the marginal portion thereof is in the form of a plate inclined at an angle to said chimney portion and to the wall of the column. The diameter of the cap, which is equal to the internal diameter of the sieve plate, is conveniently equal to one half to one third of the diameter of the column, i.e. of the sieve plate. The cap is also in the form of a chimney which, however, is closed at the top, conveniently at a point 5 to 20 cm below the top edge of the cap, by a platform. The top circular edge of the cap is advantageously provided with vertical slots (ring slots) having a width of from 0.1 to 0.5 cm and extending from the said top edge to a depth of from 1 to 6 cm said edge. These ring slots ensure uniform overflow of the liquid from the platform of the cap on all sides. The cap is advantageously also connected to the sieve plate by means of radial struts extending from the cap to the periphery of the sieve plate and having a height of, say, from 4 to 20 cm. The sieve plate may also be reinforced, if necessary, by means of further struts or ribs placed under the sieve plate. Advantageously, sieve plates are selected which have from 2,000 to 10,000 and preferably from 2,500 to 3,500 perforations per m². The diameter of the perforations is from 2 to 15 and preferably from 3 to 8 mm. The chimneys of the two plates are generally parallel to the outer wall of the column, whilst the sieve plate and the bowl-shaped lower plate are inclined at an angle to the outer wall of the column. The joint between the sieve plate and the cap is at a higher point than the joint between the sieve plate and the wall of the column, whilst the joint between the lower plate and the wall of the column is at a higher point than the joint between said plate and the associated chimney. The angle between the horizontal and the outwardly sloping sieve plate is from 2° to 10° and preferably from 3° to 5°, whilst the inwardly sloping lower plate encloses an angle of from 4° to 20° and preferably from 5° to 10° with the horizontal. The open chimney of the lower plate is usually circular in cross-section and has an internal diameter advantageously equal to from one third to one fourth of the diameter of the column. The height of the chimney is conveniently from 20 to 50 cm. If necessary, the lower plate is reinforced by annular ribs, conveniently having a height of from 4 to 20 cm, these being placed, for example, at the periphery and a point half-way between the periphery and the lower chimney. These ribs and the radial struts of the sieve plate prevent or suppress regular or irregular fluctuations or the formation of waves in the layer of liquor on the sieve plate (reciprocal motion of the liquid). The inclination gives the sieve plates and the lower plates the form of conical skirts, the surface thereof being corrugated or, conveniently, smooth.

The liquid in the form of aqueous methanol solution is preferably feed to the center of the column via the platform of the cap of the top bubble-cap sieve plate, the fed outlet being preferably from 3 to 20 cm above the center of said platform. Air is pumped into the column through a perforated tube above or below the level of the liquid at the base of the column, preferably in the zone extending from 70 cm above to 20 cm below said level, which is itself advantageously from 50 to 150 cm below the lowermost bubble-cap sieve plate.

Usually, each of the bubble-cap sieve plates has a liquid over-flow which is conveniently from 6 to 20 cm above the joint between the sieve plate and the wall of the column and which has its outlet situated above the platform of the next lower bubble-cap sieve plate. This feed of overflow liquid to the various plates takes the same form as the feed of methanol and water to the top plate. Usually, the caps for all of the plates are the same and are provided, for example, with said ring slots mentioned above. The overflow of the bottom plate has its outlet situated above the surface of the liquid in the base of the column. Advantageously, each bubble-cap sieve plate has a plurality of overflows, for example three. The heating elements, advantageously in the form of heating boxes, are disposed in the liquid at the base of the column. Evaporation is generally carried out at a temperature (at the top plate) of from 67° to 80° C and preferably from 70° to 75° C, at atmospheric pressure or, preferably, at a pressure of from 0.8 to 1.8 atmospheres, continuously or batchwise. The diagram given in the accompanying figure shows one advantageous embodiment of a bubble-cap sieve plate column of the invention having two plates. The column may be started and operated in the following manner. Liquid is passed through inlet 1 to the platform 2 of the cap 3 and sieve plate 4 and overflows through the overflow 6 to the lower sieve plate 5 and finally to the base 7 so that the platforms, sieve plates and base are filled with liquid. Each of the bubble-cap sieve plates contains a layer of liquid held by the lower bowl-shaped plate 8. The base heater 9 is then switched on and air is passed through tube 10. The air emerges through the perforated end 11 of the tube into the base 7 and passes, together with methanol and water vapors, through the chimney 12 and the layer of liquid on the lower plate through the perforations of the sieve plate 5. Due to the fact that the sieve plate 5 slopes upwardly toward the cap edge 13, the layer of liquid above the sieve plate is shallower at said edge 13 than at the column wall 14. At the commencement of operation, when the rate of vaporization is slow, gas bubbles pass through the sieve plate 5 only in the region of edge 13. As the rate of vaporization increases, the bubbles of vapor extend over an increasing area of the sieve plate 5 to pass through the same at points where the depth of liquid is greater. Thus the effective plate area increases continuously as the amount of vapor/gas increases.

By contrast, using one of the prior art bubble-cap plates, all of the bubble caps are used to the full simultaneously irrespective of the throughput. In the case of a column of the invention, a bubble-cap sieve plate of the invention is utilized to the optimum depending on the throughput. The air/vapor mixture passing from the sieve plate 5 then flows through the chimney 15, sieve plate 4 and associated layer of liquid on the upper bubble-cap sieve plate to the top 16 of the column and is thence fed to the reaction chamber.

If vaporization should be stopped for a short period, for example a period of up to 20 minutes, it is usually sufficient to restart simply by switching on the air stream. This causes evaporation of sufficient of the hot solution on the plates to enable the reactor to be restarted in a short time, for example within 30 seconds. It is an advantage that the solution retains the temperature of vaporization for a longer period, since the major portion of the solution is near the axis of the evaporator. It is advantageous to remove, occasionally or continuously, a portion of the bottoms through the outlet 17, for example from 0.006 to 0.1 ton of liquid per hour per square meter of column cross-section.

Any silver catalysts are suitable for use in the process of the invention, for example the silver catalysts described in German published application No. 1,231,229 and Ullmanns Encyklopaedie der technischen Chemie, Vol. 7, pp. 659 et seq. We prefer to use double-layer silver catalysts, for example the catalysts described in German published application No. 1,294,360 and German Patent application No. 19 03 197. For information on the manufacture of the catalyst and the method of carrying out the reaction therewith, see the cited references. One preferred embodiment of the process of the invention consists in carrying out the reaction in a double-layer catalyst in which the bottom layer has a depth of from 15 to 40 mm and in particular from 20 to 30 mm and contains at least 50% by weight of crystals having a particle size of from 1 to 4 mm and in particular of from 1 to 2.5 mm whilst the top layer has a depth of from 0.75 to 3 mm and in particular from 1 to 2 mm and contains crystals having a particle size of from 0.1 to 1 and in particular of from 0.2 to 0.75 mm, the space velocity being from 1 to 3 tons and in particular from 1.4 to 2.4 tons of methanol per square meter of catalyst bed cross-section per hour. In large-scale work, we prefer to use catalyst beds having diameter of at least 0.5 m and preferably from 1 to 3 m.

In all other respects, the oxidation is carried out in conventional manner, for example by passing the gas mixture consisting of methanol vapor, air and water vapor and optionally inert gas in the above proportions through the silver catalyst at temperatures of from about 550° to 750° C and in particular from 600° to 700° C. The reaction is generally carried out continuously at pressures of from 0.5 to 2 atmospheres and preferably from 0.8 to 1.8 atmospheres. It is advantageous to cool the reaction gases leaving the catalyst zone in a short time, for example in less than one tenth of a second, to a temperature of say 350° C. The cooled gas mixture is then conveniently passed to an absorption tower in which the formaldehyde is washed out of the gas mixture with water, preferably countercurrently.

The foremaldehyde prepared by the process of the invention is a disinfectant, tanning agent, reducing agent and valuable starting material for the manufacture of synthetic resins, adhesives and plastics, For information on its use see Ullmann, loc.cit., page 670.

In the following Examples the parts are by weight.

EXAMPLE 1

The evaporator column of a formaldehyde synthesis plant has a height of 2.9 m, as measured from the level of the bottoms, a diameter of 2.4 m and contains two bubble-cap sieve plates disposed from each at a vertical distance of 460 mm. Each bubble-cap sieve plate has an upper part in the form of a circular cap 3 with a sieve plate 4, 5 attached thereto and a lower plate 8 in the form of a shallow bowl of which the center is in the form of a round open chimney 12, 15, Whilst the marginal portion thereof is in the form of a plate inclined at an angle to said chimney portion 12, 15 and to the wall 14 of the column. The diameter of the cap, which is equal to the internal diameter of the sieve plate 4, 5, is equal to 1/2.4 of the diameter of the column. The cap 3 is also in the form of a chimney which, however, is closed at the top, at a point 12 cm below the top edge of the cap, by a platform 2. The top circular edge of the cap is provided with vertical slots having a width of 0.2 cm and extending from the said top edge to a depth of 2.5 cm below said edge. The cap is also connected to the sieve plate by means of struts extending radially from the cap 3 to the periphery of the sieve plates 4, 5 and having a height of 10 cm. The sieve plates are reinforced by further struts or ribs situated under said sieve plates.

The two sieve plates 4, 5 have 3,310 perforations per $m^2$, the diameter of the perforations being 7 mm. The side wall of the cap and that of the chimney of the lower plate 8 are parallel to the outer wall 14 of the column, whilst the seive plate 4, 5 and the bowl-shaped lower plate 8 are inclined at an angle to the outer wall 14 of the column. The joint between the sieve plate 4, 5 and the cap 3 is at a higher point than the joint between the sieve plate 4, 5 and the column wall 14, whilst the joint between the lower plate 8 and the column wall 14 is at a higher point than the joint between said plate 8 and the associated chimney 12, 15. The angle between the horizontal and the outwardly sloping sieve plate 4, 5 is 3.5°, whilst the inwardly sloping lower plate 8 encloses an angle of 7.5° with the horizontal. The open chimney 12, 15 of the lower plate 8 is circular in cross-section and has an internal diameter equal to 1/3.43 of the diameter of the column. The height of the chimney 12, 13 is 40 cm. The lower plate is reinforced by an annular rib having a height of 7 cm, this being situated at a point half-way between the column wall 14 and the lower chimney 12, 15.

The outlets of the liquid feed line 1 are 14 cm above the center of the platform 2. The air inlet 10 has a perforated tube end 11 which is 20 cm above the level of the liquid.

Each of the bubble-cap sieve plates has three liquid overflows 6 which are disposed at a height of 8 cm above the join between the sieve plate 4, 5 and the column wall 14. The overflows 6 of the top plate end above the platform of the bottom bubble-cap sieve plate. The overflows 6 of the bottom plate end above the bottoms.

The heating element 9 is in the form of a heating box and is disposed in the bottoms.

Vaporization is carried out in the evaporator column in the following manner. 3 parts/hr/$m^2$ of 60% w/w aqueous crude methanol containing 0.6% of impurities and 3.2 parts/hr/$m^2$ of air are passed to the evaporator column through the liquid inlet 1 and air inlet 10 respectively. The molar ratio of oxygen in the form of air to methanol is 0.41:1, and the molar ratio of oxygen to water is 0.345:1.

At the base outlet 17, 0.05 part of bottoms per hour per square meter of evaporator cross-section is withdrawn. 6.15 parts/hr/$m^2$ of gas mixture pass to the top 16 of the column and thence to the reaction chamber.

Evaporation is carried out continuously at a temperature of 74° C (as measured at the top bubble-cap sieve plate) and at a pressure of 1.3 atmospheres. After an on-stream period of 80 hours, the base heater is switched off and the feed of air and liquid is cut off for 20 minutes, the reaction being stopped for the same length of time. Then 0.03 part/hr/$m^2$ of air is passed into the column. The evaporator plant commences operation within 20 seconds and the reaction is reinitiated. The gas mixture of methanol vapor, air and water vapor leaves the top of the column and is passed through 0.3 part of silver catalyst to undergo reaction at 700° C.

The silver catalyst consists of two layers, of which the lower has a depth of 19 mm and consists of 94% by weight of crystals having a particle size of from 1 to 2.5 mm, whilst the upper layer has a thickness of 1.5 mm and consists of crystals having a particle size of from 0.2 to 0.74 mm. The space velocity is 2 parts of methanol per hour per $m^2$ of catalyst bed cross-section.

From 100 parts of methanol per hour there are obtained 82.5 parts of formaldehyde per hour (calculated as 100%) (88% of theory) in the form of a 90.2% w/w solution having a methanol content of 1.4% by weight. The life of the catalyst is 100 days.

EXAMPLE 2

(COMPARATIVE EXAMPLE)

An evaporator column has a height of 2.9 m above the bottoms, a diameter of 2.4 m and two sieve plate situated at a vertical distance from each other of 460 mm. The sieve plates have 3,310 perforations per $m^2$, the diameter of the perforations being 7 mm. In the center of each sieve plate there is an unperforated area (platform) having a diameter which is equal to 1/2.4 of the diameter of the column or sieve plate. The sieve plates are not inclined.

The outlets of the liquid feed line are 14 cm above the center of the platform. The air feed is effected through a perforated tube end which is 20 cm above the level of the bottoms. Each of the sieve plates has three liquid overflows disposed 8 cm above the joint between the sieve plate and the wall of the column. The overflows of the to sieve plate end above the platform of the bottom sieve plate. The overflows of the bottom sieve plate end above the bottoms.

The evaporator column is operated in a manner similar to that described in Example 1. After an on-stream period of 80 hours, the base heater is switched off and the air and liquid feeds are cut off for 20 minutes as in Example 1 and the reaction is stopped. During this period, the liquid on the sieve plates flows down to the base of the column. The liquid feed is then set at 1 part of aqueous crude methanol solution per hour per $m^2$ of column cross-section and the base heater is switched on. The concentration of methanol at the base of the column becomes 9% by weight. On account of the explosion hazard, the air feed cannot be restarted until the base liquid has been heated and evaporation has commenced. For this reason, the evaporator and reactor do not start operating until 45 minutes have elapsed. During this period, unreacted methanol passes to the absorption zone downstream of the reactor. During the next 7 hours, the 40.2% w/w aqueous formaldehyde solution formed has a content of 2.4% by weight of methanol. Due to environmental pollution problems, the off-gas has to be burned and the discharged methanol cannot be reused. Within 2 hours, the liquid feed is readjusted to 3 parts/hr/m$^2$ of aqueous crude methanol solution and the air feed is set as in Example 1. The reaction is carried out as described in Example 1 and gives a yield of 86.3% of theory. The life of the catalyst is 70 days.

We claim:

1. In a process for the manufacture of formaldehyde by oxidative dehydrogenation of methanol in admixture with water vapor and air and in the presence of a silver catalyst at elevated temperature, the improvement which comprises purifying the methanol and supplying the purified methanol, water vapor and air mixture to the catalyst for said oxidative dehydrogenation which comprises:

evaporating the methanol and water in a rectifying plate column in which said crude methanol and water as liquids are fed to the top and the air to the bottom of the column;

carrying out rectification by refluxing liquid by overflow from an upper plate assembly to a lower plate assembly and from the lowermost plate assembly to a liquid bottoms while supplying heat substantially only to said liquid bottoms to evaporate methanol for conduction with air and water vapor as a countercurrent gas upwardly through said column;

directing the liquids fed to each plate assembly as an individual rectifying zone such that the liquids flow first over a central bubble cap platform area, then to a lower surrounding sieve plate joined to said platform and finally to an annular retaining and overflow zone on a second plate joined below each sieve plate from which the liquid is conducted to the next lower rectifying zone or to said liquid bottoms, the coutercurrent gas flowing upwardly through each sieve plate for intimate contact with the liquid flowing therein;

withdrawing a liquid bottoms fraction from said plate column as an impure waste material substantially free of methanol; and recovering a vaporous fraction from the top of said column consisting essentially of gaseous methanol, water vapor and air as a feed stream for said oxidative dehydrogenation.

2. A process as claimed in claim 1, wherein evaporation is carried out at throughputs of from 1.2 to 5.0 tons of aqueous methanol solution and 1.3 to 5.5 tons of air per hour per square meter of column cross-section and the reaction is carried out at molar ratios of from 0.25 to 0.60 moles of oxygen (in the form of air) per mole of methanol and from 0.2 to 2 moles of oxygen (in the form of air) per mole of water.

3. A process as claimed in claim 1, wherein evaporation is carried out with air introduced into a zone extending from 70 cm above to 20 cm below the level of the bottoms.

4. A process as claimed in claim 1 wherein the evaporation is carried out at a temperature of the top plate assembly of from 67° to 80° C. and at a pressure of from 0.8 to 1.8 atmospheres.

5. A process as claimed in claim 1 wherein the evaporation is carried out at a temperature of the top plate assembly of from 70° to 75° C.

6. A process as claimed in claim 1 wherein the liquids in an individual rectifying zone are directed to flow at an angle of slope to the horizontal of from 2° to 10° over said sieve plate and then from 4° to 20° over said second plate.

7. A process as claimed in claim 6 wherein the liquids in an individual rectifying zone flow first in a horizontal direction over said central bubble cap platform area.

* * * * *